US009096647B2

(12) United States Patent
Olma et al.

(10) Patent No.: US 9,096,647 B2
(45) **Date of Patent: *Aug. 4, 2015**

(54) SIMPLIFIED ONE-POT SYNTHESIS OF [$^{18}$F]SFB FOR RADIOLABELING

(71) Applicant: The Regents of the University of California, Oakland, CA (US)

(72) Inventors: Sebastian Olma, Muenster (DE); Clifton Kwang-Fu Shen, Archerfield (AU)

(73) Assignee: The Regents Of The University Of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,397

(22) Filed: Jun. 21, 2013

(65) Prior Publication Data

US 2013/0289249 A1 Oct. 31, 2013

Related U.S. Application Data

(63) Continuation of application No. 13/063,741, filed as application No. PCT/US2009/005176 on Sep. 16, 2009, now Pat. No. 8,487,077.

(60) Provisional application No. 61/097,463, filed on Sep. 16, 2008, provisional application No. 61/116,527, filed on Nov. 20, 2008.

(51) Int. Cl.

| | |
|---|---|
| ***C07D 207/46*** | (2006.01) |
| ***C07D 207/444*** | (2006.01) |
| ***C07K 1/13*** | (2006.01) |
| ***C07D 207/26*** | (2006.01) |

(52) U.S. Cl.

CPC ................ *C07K 1/13* (2013.01); *C07D 207/26* (2013.01); *C07D 207/444* (2013.01); *C07D 207/46* (2013.01)

(58) Field of Classification Search

CPC .......................... C07D 207/46; C07D 207/444

USPC .............. 530/317, 325, 328, 329, 331, 391.3, 530/389.1

See application file for complete search history.

(56) References Cited

U.S. PATENT DOCUMENTS

2007/0276231 A1 11/2007 Low et al.

FOREIGN PATENT DOCUMENTS

| | | | |
|---|---|---|---|
| EP | 2123667 | A1 | 11/2009 |
| WO | WO2008/098112 | A2 | 8/2008 |
| WO | WO2008/108242 | A1 | 9/2008 |

OTHER PUBLICATIONS

S.M. Okarvi, Recent Progress in fluorine-18 labelled peptide radiopharmaceuticals, Eur J Nucl Med (2001) 28; 929-938.*

R. Paramashivappa et al., Synthesis of sildenafil Analogues from Anacardic Acid and Their Phosphodiesterase-5 Inhibition J. Agric. Food. Chem. 2002, 50, 7709-7713.*

Supplemental European Search Report and the European search opinion of corresponding EP Patent Application No. 09814890.1 mailed Jul. 2, 2012.

Tang G. et al., "Facile synthesis of N-succinimidyl 4-[F-$^{18}$]fluorobenzoate ([F-$^{18}$]SFB) for protein labeling", Journal of Labelled Compounds and Radiopharmaceuticals, John Wiley, Chichester, GB, vol. 51, No. 1-2, Jan. 1, 2008, p. 68-71, XP002503973.

F. Wust et aI., Radiolabelling of isopeptide N-(y-glutamyl)-I-Iysine by conjugatiion with N-succinimidyl-4-[18F]fluorobenzoate, Applied Radiation and Isotopes 59, 43-48, 2003.

R. Raramashivappa et aI. Synthesis of sildenafil Analogues from Anacardic Acid and Their Phosphodiesterase-5 Inhibition J. Agric. Food. Chem. 2002, 50, 7709-7713.

* cited by examiner

*Primary Examiner* — Michael G Hartley

*Assistant Examiner* — Jagadishwar Samala

(74) *Attorney, Agent, or Firm* — Koppel, Patrick, Heybl & Philpott; Michael J. Ram

(57) ABSTRACT

A non-aqueous single pot synthesis of [$^{18}$F]SFB is set forth. The [$^{18}$F]SFB produced with this method is then used, for example, to label a peptide or an engineered antibody fragment (diabody) targeting human epidermal growth factor receptor 2 (HER2) as representative examples of labeled compounds for use as an injectable composition to locate abnormal tissue, specifically tumors within an animal or human using a PET scan.

19 Claims, 7 Drawing Sheets

Figure 1:
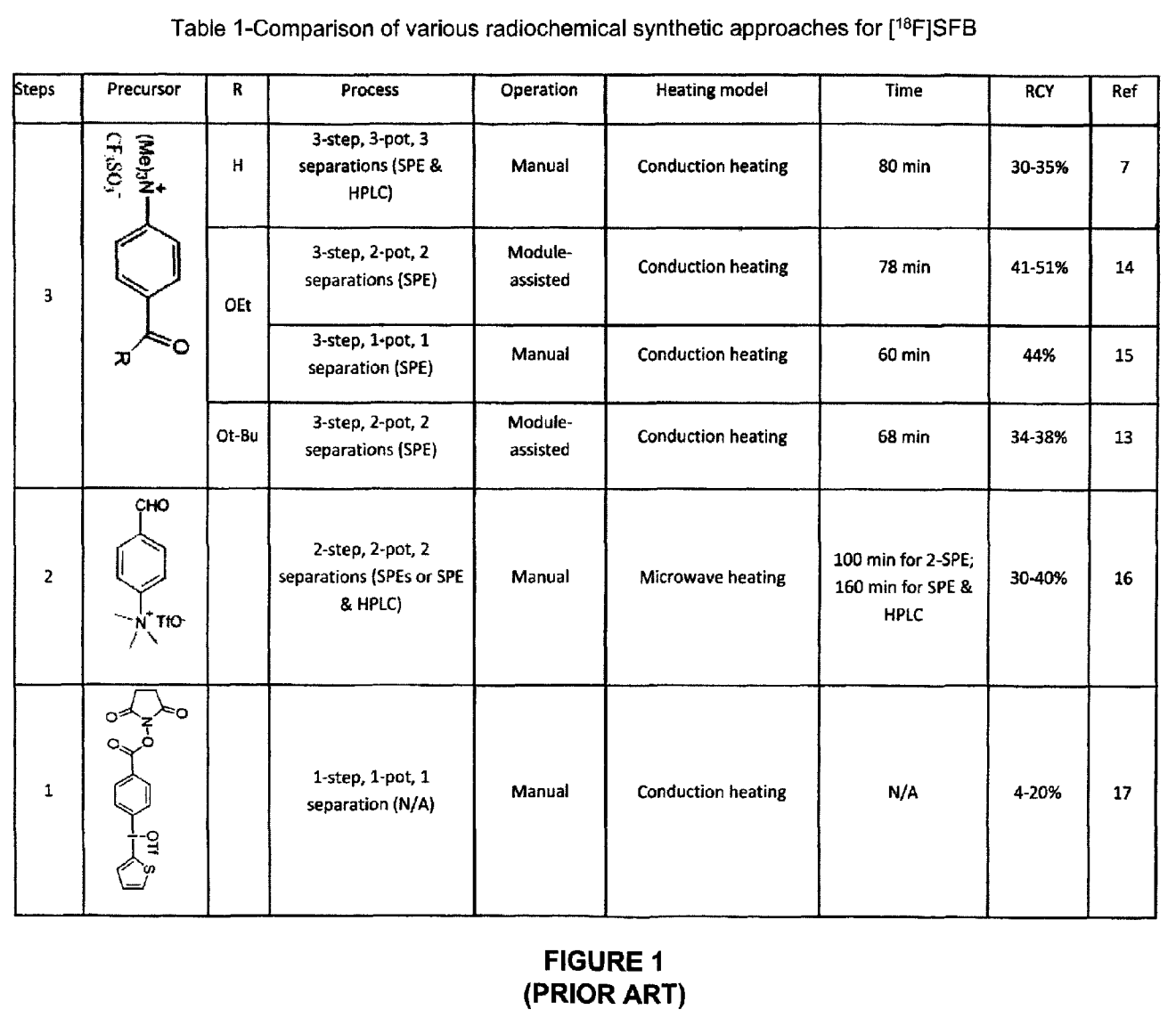

Table 1-Comparison of various radiochemical synthetic approaches for [$^{18}$F]SFB

| Steps | Precursor | R | Process | Operation | Heating model | Time | RCY | Ref |
|---|---|---|---|---|---|---|---|---|
| 3 | $(Me)_3N^+$ $CF_3SO_3^-$ … R | H | 3-step, 3-pot, 3 separations (SPE & HPLC) | Manual | Conduction heating | 80 min | 30-35% | 7 |
| | | OEt | 3-step, 2-pot, 2 separations (SPE) | Module-assisted | Conduction heating | 78 min | 41-51% | 14 |
| | | | 3-step, 1-pot, 1 separation (SPE) | Manual | Conduction heating | 60 min | 44% | 15 |
| | | Ot-Bu | 3-step, 2-pot, 2 separations (SPE) | Module-assisted | Conduction heating | 68 min | 34-38% | 13 |
| 2 | CHO … $N^+$ TfO$^-$ | | 2-step, 2-pot, 2 separations (SPEs or SPE & HPLC) | Manual | Microwave heating | 100 min for 2-SPE; 160 min for SPE & HPLC | 30-40% | 16 |
| 1 | N-O … I … OTf … S | | 1-step, 1-pot, 1 separation (N/A) | Manual | Conduction heating | N/A | 4-20% | 17 |

SIMPLIFIED ONE-POT SYNTHESIS OF [$^{18}$F]SFB FOR RADIOLABELING

This is a Continuation of U.S. application Ser. No. 13/063,741 filed Apr. 29, 2011 which is a US National Stage application of International Application PCT/US2009/05176 filed Sep. 16, 2009 and claims benefit of U.S. Provisional Application Ser. No. 61/097,463 filed Sep. 16, 2008 and U.S. Provisional Application Ser. No. 61/116,527 filed Nov. 20, 2008.

This invention was made with Government support under CA086306, awarded by the National Institutes of Health; DE-FG02-06ER64249, awarded by the United States Department of Energy. The Government has certain rights in this invention.

FIELD OF INVENTION

Preparation of $^{18}$F-labeled moieties using an anhydrous saponification method and biomolecules labeled with F-18 for use in targeting diseased tissue within an animal, including the human body, are described.

BACKGROUND OF THE INVENTION

PET (Positron Emission Tomography) is a powerful non-invasive molecular imaging technology which provides sufficient sensitivity to visualize and quantitate in vivo physiological interactions in a volume- and target-depth independent manner. PET has been widely used clinically to detect various diseases, such as cancer, cardiovascular disease, and neurodegenerative disease, non-invasively. With a specific positron-emitter labeled molecular probe, PET can reveal the status of specific physiological and biochemical function of living organisms. The system detects pairs of gamma rays emitted at approximately 180 degrees to each other in the event of positron annihilation. With information obtained, three-dimensional images of tracer location and concentration can be reconstructed mathematically to visualize the physiological and functional changes of biological system of interest within the body.

PET tracers are chemical and/or biological molecules labeled with short-lived positron emitting isotopes. The PET tracer is injected into the animal or human body just before scanning. The tracer travels through the body to a target site and its emitted position reveals information about the target receptor density, target protein distribution or specific biological functions, such as metabolism of the radiolabeled molecule. Various PET tracers have been developed to interact with different biological targets and entities according to their biological mechanism in vivo. Some of them have become clinically available and have proven to be useful for disease diagnosis and monitoring therapeutic efficacy, such as $^{18}$F-labeled PET tracers (e.g. [$^{18}$F]FDG, [$^{18}$F]FLT, and [$^{18}$F]FDOPA) and $^{11}$C-labeled PET tracers (e.g. [$^{11}$C]acetate, [$^{11}$C]choline, and [$^{11}$C]methioine).

Among the available PET radionuclides, fluorine-18 (F-18) is the most widely used in clinical settings. The half-life of C-11 is very short (only 20.4 min) while F-18 has a longer half-life (110 min). F-18 labeled compounds are more desirable because this longer half life allows multi-step radiochemical manipulations as well as in vivo biological studies that can last for several hours. These unique features make fluorine-18 a very attractive isotope for PET imaging because of its ease for mass production using a biomedical cyclotron, well-established synthesis procedures to incorporate F-18 into desired structures, and high-spatial resolutions of resulted images due to its low positron energy. In addition, its high positron abundance and nearly monochromatic emission lead to simplified detection, data processing and greater sensitivity. F-18 is also preferred for the development of novel PET tracers because it is available in high specific activity. The flexibility of fluorine-18 chemistry not only produces large amounts of useful PET tracers originated from small organic molecules but also has potential to turn certain highly-specific targeting biological molecules, such as proteins or peptides (Annexin V, VIP, RGD, anti-CEA diabody, etc.) into valuable PET tracers.

Biomolecules, such as peptides, proteins, antibodies, diabodies, minibodies and others have gained importance as a role in PET tracers. They serve not only as potential therapeutics but also PET imaging probes once labeled with positron-emitters, e.g. F-18. The concept of applying radiolabeled biomolecules to target receptor-(over)expressed tissues in vivo has opened up a new avenue for immunoPET as a very useful diagnostic tool to visualize tumor lesions. However, because of the harsh chemical conditions associated with direct radiofluorination that is usually not compatible with most biological samples, the incorporation of radionuclide-tagged prosthetic groups into biomolecules becomes the method of choice.

However, the widespread use of $^{18}$F-labeled biomolecules such as peptides and proteins for positron emission tomography (PET) is hampered by the limited availability of suitable labeling tags like N-succinimidyl 4-[$^{18}$F]fluorobenzoate ([$^{18}$F]SFB), also identified as in the Figures as [$^{18}$F]4. Because [$^{18}$F]SFB can react with primary amines of biomolecules, it has been demonstrated to be a suitable and versatile $^{18}$F-prosthetic group to radiolabel peptides, proteins, and antibodies in terms of in vivo stability and radiolabeling yield. However, the tedious synthesis procedures to obtain this compound set forth in the prior art hamper its widespread use for radiolabeling biomolecules as PET probes. Several prior available representative procedures of preparing [$^{18}$F]SFB are summarized in Table 1 (FIG. 1).

Most of the radiochemical syntheses of [$^{18}$F]SFB described in the literature require two to three reactors and multiple SPE or HPLC purifications. Referring to FIG. 2, Two previously described precursors, (4-ethoxycarbonyl-phenyl) trimethylammonium triflate (1a) (Wester H J, Schottelius M. Fluorine-18 Labeling of Peptides and Proteins. *PET Chemistry—The Driving Force in Molecular Imaging*, Schubiger P A (ed), Lehmann L (ed), Friebe M (ed). Springer: Berlin Heidelberg, (2007); Haka M S, Kilbourn M R, Watkins G L, Toorongian S A. *J Label Compd Radiopharm;* 7: p 823-833 (1989); Guhlke S, Coenen H H, Stöcklin G. *Appl Radiat Isot;* 45, p 715-727 (1994) and (4-tert-butoxycarbonyl-phenyl)trimethylammonium triflate (1b) (Wester H J, Hamacher K, Stöcklin G. *Nucl Med Biol,* 23, p 365-372 (1996); Hostetler E D, Edwards W B, Anderson C J, Welch M J *J Label Compd Radiopharm,* 42, p S720-S722 (1999), were compared in terms of radiochemical yield (RCY) and chemical as well as radiochemical purity. This comparison was repeated after the deprotection step in both pathways. It was found that the use of 1a was superior to 1b.

Although module-assisted [$^{18}$F]SFB production in various semi-automated synthesizers has been reported, there are still several drawbacks for its general use. In particular, the need for two solid phase extraction (SPE) steps with three different cartridges as published by Wester et al. 6. (Wester H J, Schottelius M. *Fluorine*-18 *Labeling of Peptides and Proteins. PET Chemistry—The Driving Force in Molecular Imaging*, Schubiger P A (ed), Lehmann L (ed), Friebe M (ed). Springer: Berlin Heidelberg, (2007); Wester H J, Hamacher K, Stöcklin G. *Nucl Med Biol,* 23, p 365-372 (1996)) is very demanding. Various implementations include modifications of commercial synthesizers to perform the SPE steps. These hardware and software changes make it difficult for labs lacking engineering expertise and facilities to repeat the procedures. Recently, Kabalka et al. (Kabalka G, J Label *Compd Radiopharm,* 51, p 68-71 (2008)) described an efficient preparation of [$^{18}$F]SFB based on a three-step, one-pot procedure. The entire process takes about 60 minutes and the deprotection/hydrolysis step is carried out with an aqueous tetrapropylammonium hydroxide solution. Subsequent time-consuming azeotropic drying is necessary due to the application of aqueous reagent. Another approach published by Carroll et al. (Carroll M, *J Nucl Med,* 49(S): p 298P (2008)) is to utilize iodonium salt precursor for preparing [$^{18}$F]SFB in a one-step, one-pot procedure. Although it is a very attractive route, the overall yield is low and the precursor is also unstable. Therefore, further improvement and simplifying [$^{18}$F]SFB synthesis would be very beneficial for use in an automated process.

SUMMARY

A non-aqueous single pot synthesis of [$^{18}$F]SFB is set forth. The [$^{18}$F]SFB produced with this method is then used, for example, to label a peptide or an engineered antibody fragment (diabody) targeting human epidermal growth factor receptor 2 (HER2) as representative examples of labeled compounds for use as an injectable composition to locate abnormal tissue, specifically tumors within an animal or human using a PET scan.

BRIEF DESCRIPTION OF DRAWINGS

FIG. 1 is a table comparing the characteristics of prior art reactions using five different precursors with different preparative steps.

FIG. 9 is a time series of micro-PET/CT images of a 1 hour dynamic scan of a nude mouse bearing MCF-7/HER2 xenograft (coronal (top) and transverse (bottom)) views on each set. The times of the imaging frames are shown in seconds. The triangular mark indicated the location of the tumor.

DETAILED DESCRIPTION

Figure 2:
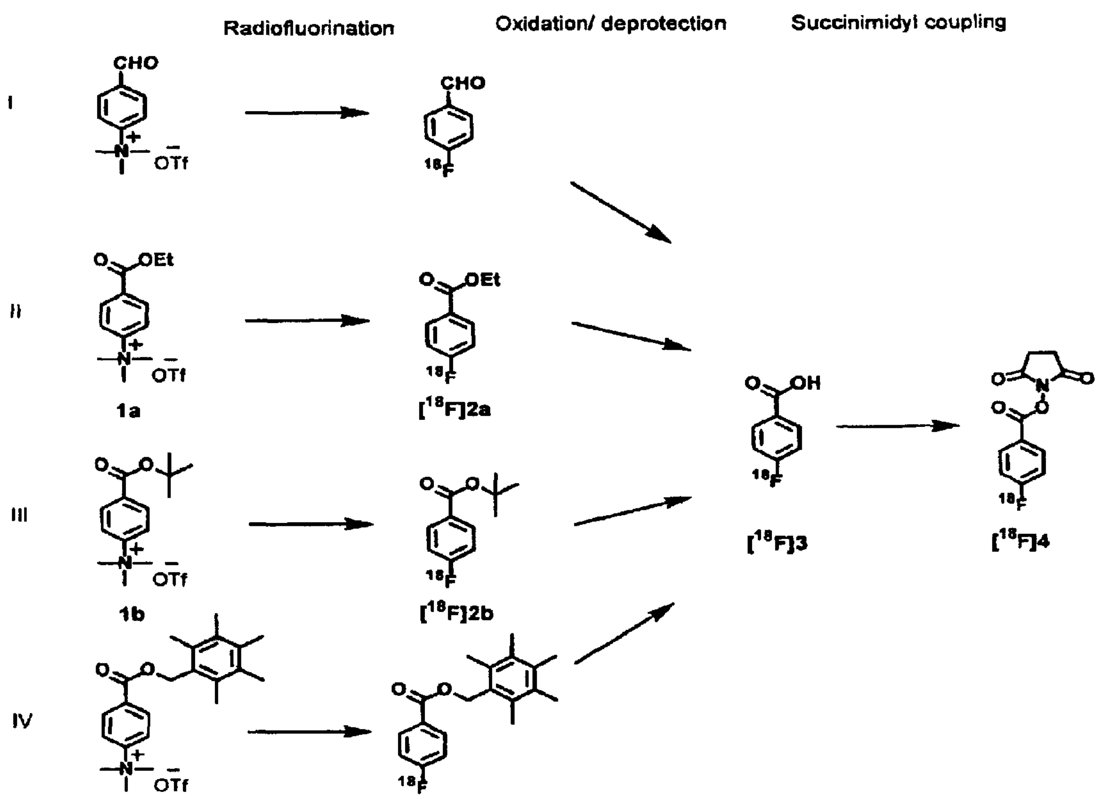
FIG. 2 shows four representative reaction schemes used to prepare [$^{18}$F]SFB.

Typical prior art radiosynthesis of [$^{18}$F]SFB comprises three steps with a total synthesis time of about 90-120 minutes. Additional labeling and purification of the final biomolecule tracers makes the entire procedure time-consuming and very complex. Only individuals with access to radiochemistry facility and personnel with radiochemistry expertise can perform studies regularly using [$^{18}$F]SFB. The prior art general approach to synthesis of [$^{18}$F]SFB can be performed in one or two reactors. However, most of the published processes require several cartridge or HPLC purification steps. Additionally, an azeotropic distillation drying step is necessary for most procedures, because an aqueous solution is generally used for deprotection/saponification reaction. In the single vessel procedure described by Kabalka et al, the vessel must be cleaned out and moisture eliminated using azeotropic drying before activation/N-hydroxylsuccinimide (NHS) ester formation. A simplified synthesis of [$^{18}$F]SFB with short synthesis time and comparable radiochemical yield is therefore highly desirable.

All prior described radiosyntheses use an aqueous basic solution for the deprotection of the first intermediate alkyl 4-[$^{18}$F]fluorobenzoate to obtain the corresponding 4-[$^{18}$F]fluorobenzoate. The water in this solution is incompatible with the next following reaction with O-(N-succinimidyl)-N,N,N',N'-tetramethyluronium tetrafluoroborate (TSTU) used to form [$^{18}$F]SFB. Therefore the reaction mixture has to be dried. This is usually accomplished by azeotropic distillation of the eluate of the SPE or passing it through a sodium sulphate cartridge.

Described herein is an anhydrous system which can be applied to all these approaches for the deprotection strategy of ethyl 4-[$^{18}$F]fluorobenzoate ([$^{18}$F]2). The utilization of potassium tert-butoxide (t-BuOK) in dimethylsulfoxide (DMSO) eliminates the need for water and the final basicity of the resulting solution is sufficient to catalyze the coupling of the N-hydroxysuccinimide moiety with TSTU.

The [$^{18}$F]SFB produced can then be purified by SPE on a Merck EN cartridge and eluted with diethyl ether. After evaporation of the solvent, [$^{18}$F]SFB is dissolved in an aqueous buffer and a solution of the peptide or diabody is added for labeling. For the short peptides labeled according to the invention set forth herein, the purification of the radiotracer is performed via reversed phase HPLC on a standard semi-preparative C18 column, and the volume of the product solution is reduced by rotary evaporation. For a diabody, the purification is carried out using a microspin column. The eluate is directly used for in vitro or in vivo studies.

In contrast to prior aqueous reaction schemes, the present invention comprises an efficient anhydrous deprotection process so that the [$^{18}$F]SFB synthesis can be performed in a single reactor without the need for azeotropic drying in-between. In addition, the applied base can readily catalyze the final activation of [$^{18}$F]3. Several aspects of previously published procedures improved by the present invention are (1) the application of anhydrous reagent for the deprotection step, thus eliminating the need of SPE separation of intermediate compounds and the corresponding removal of solvent via evaporation and (2) the use of microwave energy to accelerate the reaction and shortening synthesis time.

Figure 3:
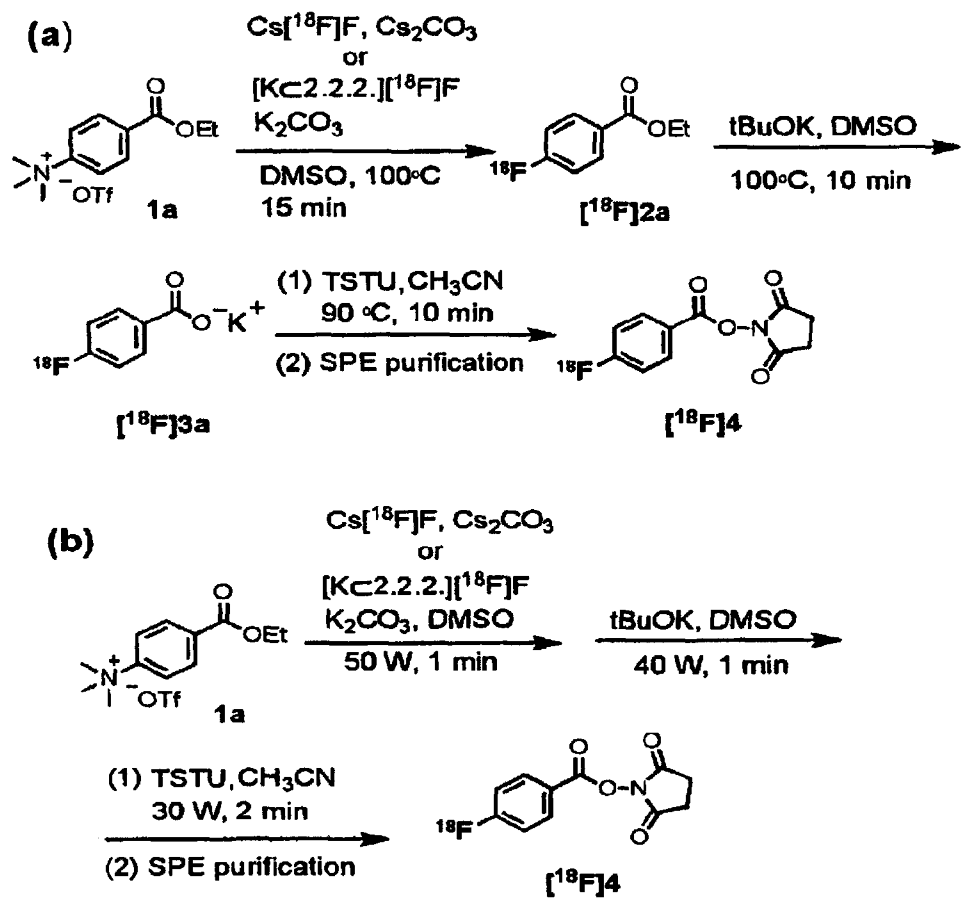
FIG. 3 sets forth reactions for the synthesis of [$^{18}$F]SFB using a one-pot process incorporating features of the invention.

A radiosynthesis procedure incorporating features of the invention follows the procedure depicted in reaction scheme shown in FIG. 3. In the presence of carbonate ions as base, a alkyl or aryl 4-trimethylammoniumbenzoate triflate precursor such as ethyl 4-trimethyl-ammonium-benzoate triflate 1a is reacted at 100° C. for 15 minutes with the dried potassium- Kryptofix-2.2.2 complex salt of [$^{18}$F]fluoride in DMSO. Examples of suitable alkyl groups include, but are not limited to methyl, ethyl, i-propyl, benzyl, etc. and suitable aryl groups include, but are not limited to phenyl or substituted phenyls. As an alternative to the Kryptofix system, cesium carbonate can be used as a source of the activating counter ion for [$^{18}$F]fluoride, and it can also acts as a base to enable the labeling and activation reactions. After the radiofluorination is complete, a solution of a basic anhydrous/aprotic solvent is added and the reaction vessel is heated again. Examples of suitable anhydrous/aprotic solvents include, but are not limited to t-BuOK in anhydrous DMSO, LiCl in DMF or pyridine, NaCN in DMSO, $KO_2$, 18-crown-6 in benzene, LiCl in EtOAc, TMSCl or NaI in MeCN, $MgI_2$ in toluene, and $(Bu_3Sn)_2O$ in benzene. The deprotection step is performed at 100° C. for 10 minutes. Finally, a solution of an activating agent, for example, O—N-succinimidyl)-N,N,N',N'— in acetonitrile, (TSTU in MeCN) is added to the reaction mixture contained 4-[$^{18}$F]fluorobenzoate. After heating at 90° C. for 10 minutes [$^{18}$F]SFB is obtained. In addition, the entire process can be further shortening and sped up by utilizing microwave energy/heating (See Scheme (b) in FIG. 3).

Once the [$^{18}$F]SFB is formed it can be used to label peptides or proteins. As an example, labeling of a short peptide targeting human epidermal growth factor receptor 2 (HER2) is described below.

Human epidermal growth factor receptor 2 (HER2) is an important biomarker because it is over-expressed in a notable percentage of breast cancer diseases. It has been reported in the literature that a short peptide sequence (KCCYSL) can bind specifically to HER2 both in vitro and in vivo. In that case the peptide was radiolabeled by a chelating linker with indium-111 for single photon emission computed tomography (SPECT) in mice. To label HER2 with [$^{18}$F]SFB the amino acid sequence KGSG was added to the binding part KCCYSL to offer an anchor for fluorine-18 labeling. Fluorine-18 can be bound to this anchor via the reaction of [$^{18}$F]SFB with the primary amine of the lysine in the molecule to form an amide bond. This reaction has been proven to be the method of choice for radiofluorination of biomolecules.

A novel feature of the described radiosynthesis of [$^{18}$F]SFB is the anhydrous deprotection strategy that supersedes two SPE units and one drying steps in-between and enormously reduces its overall complexity. The shortened overall synthesis time also results in increased specific activity of the final probe, an important parameter that affects the quality of assays or imaging performed with labeled probes. The radiochemists can also work with much lower levels of starting radioactivity and still achieve the same final activity level (because the time for radioactive decay is reduced). Reduced complexity also enables a broader range of investigators to use this probe on a routine basis. Further, the simpler synthesis is much easier to automate. In addition, the use of the microwave module enables fast, reliable and automated production of this important fluorine-18 labeling tag.

Figure 4:
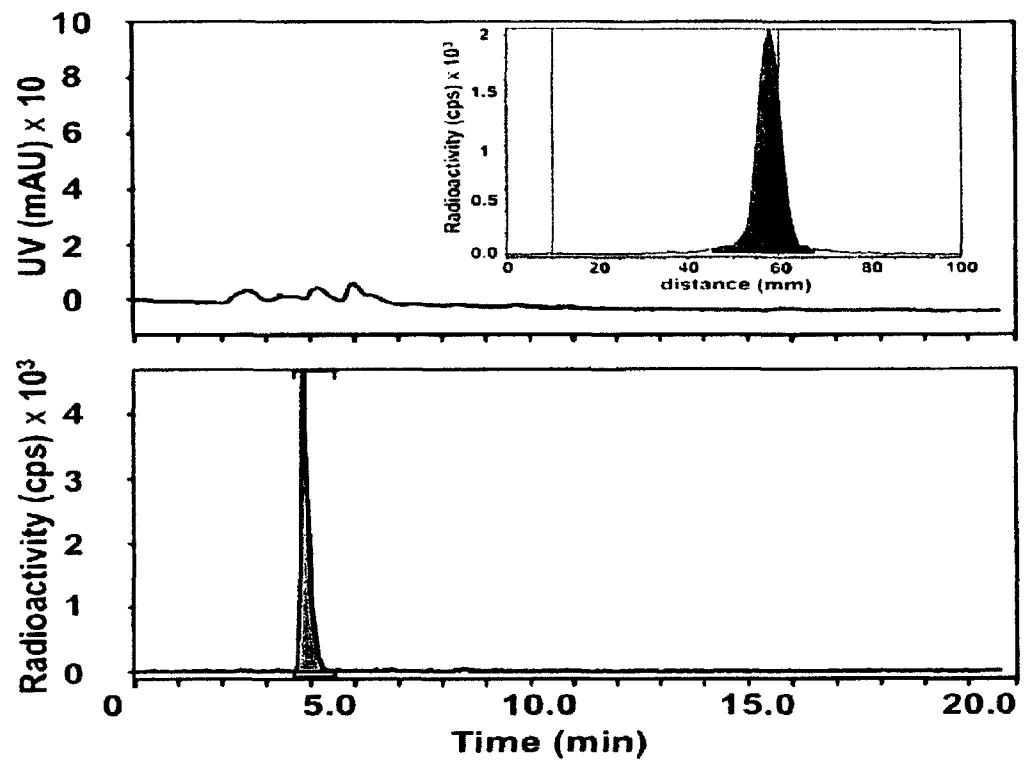
FIG. 4 shows liquid HPLC and radio-TLC (the smaller inserted graph) chromatograms illustrating an analysis of [$^{18}$F]SFB prepared in accordance with the synthesis shown in FIG. 3.

The modified procedures operated at optimized conditions leads to RCY and radiochemical purity of [$^{18}$F]SFB which are at least comparable to those described in the literature for prior procedures. In addition, the chemical purity of [$^{18}$F]SFB was optimized to provide the UV absorption curve and the high-performance liquid (HPL) chromatogram shown in FIG. 4. Besides improvements of radiochemical yield and purity, automation of the processes allows scale up of the amount of radioactivity used and makes [$^{18}$F]SFB more accessible. The higher amount of radioactivity is necessary because [$^{18}$F]SFB is only the $^{18}$F-tag for radiolabeling of biomolecules, and the final labeling step of biomolecules often shows low radiochemical yields. In addition, the described process has a great reproducibility and can be reliably used for [$^{18}$F]SFB routine production.

The improved and concise synthesis makes routine production of [$^{18}$F]SFB much more practical and attractive for non-radiochemists. It is believed that biomedical discovery and clinical studies using $^{18}$F-labeled biomolecules as a research tool will accelerate if [$^{18}$F]SFB can be more widely available and used. A great number of biologists and clinicians could benefit from the ability to incorporate $^{18}$F-labeling onto a variety of biomolecules. In addition, commercial radiopharmacies, such as PETNET, already provides a network of sources of inexpensive F-18 ion and, in combination with an automated approach to make [$^{18}$F]SFB from the process described herein, the usage can be greatly expanded. The procedures set forth herein can be applied to a fully automated system to perform the [$^{18}$F]SFB synthesis and can lead to the development of various $^{18}$F-labeled biological probes for preclinical or clinical studies in animals or humans.

EXAMPLE 1

One-Pot Synthesis of N-Succinimidyl 4-[$^{18}$F]fluorobenzoate ([$^{18}$F]SFB) Using Conventional Heating No-carrier-added [$^{18}$F]fluoride was produced from the nuclear reaction $^{18}O(p,n)^{18}F$ by irradiation of 97% $^{18}$O-enriched water with an 11 MeV proton beam using RDS-112 cyclotron (Siemens Medical Solution, Knoxville, Tenn.). 10 to 50 μl (37-370 MBq) of aqueous [$^{18}$F]fluoride solution in [$^{18}$O]$H_2O$ was mixed with 10 mg (26.6 μmol) of Kryptofix 222 ($K_{222}$), 13 μl of 1M of aqueous $K_2CO_3$ solution and 1 ml of anhydrous MeCN (biotech grade) was then added into a V-vial (Wheaton (Millville, N.J.)) closed with a silicon septum in an oil bath preheated to 90° C. The mixed solution was heated at 90° C. for 5 min and a vacuum suction (800 mbar) was applied to remove the water by azeotropic evaporation until the mixture was dry. After cooling down to room temperature, 1 ml of anhydrous MeCN was added into the vial and the azeotropic evaporation was repeated using the same conditions as above to produce the anhydrous ([K⊂2.2.2][$^{18}$F]F salt. The radiochemical yield for this labeling step is between 80 and 90% after 20 min of evaporation.

After cooling to room temperature, 3 mg of ethyl 4-trimethylammoniumbenzoate triflate in 0.3 ml of anhydrous DMSO (300 μL) was added into the vial containing the dried $K_{222}$/[$^{18}$F]F and the mixture was heated at 100° C. for 15 min to produce ethyl 4-[$^{18}$F]fluorobenzoate. After cooling, 10 mg (89.1 μmol) of t-BuOK in 0.3 ml of anhydrous DMSO was added into the vial and heated at 100° C. for 10 min to perform the deprotection of ethyl ester to produce potassium 4-[$^{18}$F]fluorobenzoate (deprotecting step). After cooling down, a solution of 20 mg of TSTU in 2.5 ml of anhydrous MeCN was added and then heated at 90° C. for 10 min to produce [$^{18}$F]SFB (coupling step). After cooling, 1 ml of 5% aqueous acetic acid was injected into the vial to quench the reaction and then the total reaction mixture was transferred into a 25 ml syringe which also contained 8 ml of 5% aq. AcOH under the positive pressure of nitrogen (15~20 psi) to dilute the mixture. The diluted solution was passed through a Merck EN cartridge (200 mg) preconditioned with 10 ml of EtOH and 10 ml of 5% aq. AcOH under the positive pressure of $N_2$ (5-10 psi). The cartridge was then washed using 10 ml of the mixed solvent of MeCN/$H_2O$ (v/v, ½). Finally, the trapped [$^{18}$F]SFB was eluted from the cartridge using 3 ml of ethyl ether and collected into another V-vial placed into a water bath (30° C.). The ether solvent was removed with a gentle blowing of $N_2$ and stirring. 100 to 200 μl of PBS (pH 7.4) was added to the composition remaining after the ether removal to redissolve [$^{18}$F]SFB. The final solution of [$^{18}$F]SFB in PBS (pH 7.4) was directly used for the subsequent labeling of HER-2 targeting peptides or a HER-2 diabody.

The above description sets forth one set of operating conditions. One skilled in the art will recognize that the operating conditions can be varied to optimize each step of the reaction and that variations in these operating conditions can result in slight differences in yield and quality of the end product. For example, with reference to the operating conditions in this Example 1, alternative reaction temperatures and times for labeling are 90-100° C. for 5-15 minutes, deprotection are from about 90° C. to about 100° C. for about 5-10 minutes and the coupling step is performed at 85° C.-90° C. for about 9-10 minutes. Further, other weak acidic aqueous solutions can be used in place of the 5% aq. acetic acid and the eluent can be an organic solvent other than ethyl ether.

EXAMPLE 2

One-Pot Synthesis of [$^{18}$F]SFB from Microwave Heating

The microwave cavity of a commercially available microwave system (Discover; CEM, Matthew, N.C.) was modified to receive a 5 mL Wheaton V-vial, said vial equipped with a magnetic stir bar and PEEK lid with tubing connections extending into the vial. This remote controlled radiochemical setup utilizes seven electrically switched solenoid valves which were connected to the V-vial via a PEEK adapter through 1/16" Teflon tubing. Three valves were used to control reagent delivery through tubing equipped with a Luer adapter. One port served as a solution output, with the tubing in that port extending to the bottom of the vial. Another port provides venting of the vial. One of the remaining ports is connected to pressurized nitrogen; the second remaining port is connected to a vacuum pump. The CEM Synergy software was used to control the operation of the microwave cavity.

10 to 50 μl of aqueous [$^{18}$F]fluoride solution in [$^{18}$O]$H_2O$ was mixed with 10 mg (26.6 μmol) of Kryptofix 222 ($K_{222}$), 13 μl of 1M of aqueous $K_2CO_3$ solution and 1 ml of anhydrous MeCN and then transferred into a V-vial (Wheaton) placed into the microwave cavity. A vacuum was applied to the mixed solution and it was exposed to 20 W power for 3 min using a microwave synthesizer (CEM Discover) to remove the water by azeotropic evaporation. After cooling down to room temperature using a strong blowing of cooling air, 1 ml of anhydrous MeCN was added into the vial. The azeotropic evaporation was repeated again using the same conditions to produce an anhydrous $K_{222}$/[$^{18}$F]F complex.

After cooling down to room temperature, 3 mg of ethyl 4-trimethylammoniumbenzoate triflate in 0.3 ml of anhydrous DMSO was added into the vial of the dried $K_{222}$/[$^{18}$F]F and the mixture was exposed to 50 W of microwave energy for 1 min to produce ethyl 4-[$^{18}$F]fluorobenzoate (labeling step). After cooling, 10 mg (89.1 μmol of t-BuOK dissolved in 0.3 ml of anhydrous DMSO was added into the vial and exposed to 40 W power for 1 min to perform the deprotection step to produce potassium 4-[$^{18}$F]fluorobenzoate. After cooling, a solution of 20 mg of TSTU in 2.5 ml of anhydrous MeCN was added into the vial and then exposed to 30 W power for 2 min to conduct the coupling reaction and produce [$^{18}$F]SFB. After cooling, 1 ml of 5% aqueous acetic acid was injected into the vial to quench the reaction and then, to dilute the mixture, the total reaction mixture was transferred into a 25 ml syringe reservoir also containing 8 ml of 5% aq. AcOH under the positive pressure of nitrogen (15-20 psi). The diluted solution was passed through an EN cartridge (Merck) preconditioned with 10 ml of EtOH and 10 ml of 5% aq. AcOH under the positive pressure of $N_2$ (5-10 psi). The cartridge was washed using 10 ml of MeCN/$H_2O$ (v/v, ½) mixed solvent. Finally, the [$^{18}$F]SFB trapped in the cartridge was eluted out using 3 ml of ethyl ether and collected into another V-vial placed into a water bath (30° C.). The ether solvent was removed with a gentle blowing of $N_2$ and stirring. 100 to 200 μl of PBS (pH 7.4) was added to the residual remaining after the removal of the ether to redissolve the [$^{18}$F]SFB. The final solution of [$^{18}$F]SFB in PBS (pH 7.4) was then used for the subsequent labeling of peptides or diabodies.

The above description sets forth one set of operating conditions. One skilled in the art will recognize that the operating conditions can be varied to optimize each step of the reaction and that variations in these operating conditions can result in slight differences in yield and quality of the end product. For example, with reference to the operating conditions in this Example 2, alternative levels of microwave energy provided to the reaction vessel and times for the labeling step are 20 W-60 W for 1-3 min, for the deprotection step are from about 40 W-50 W for about 1 minute and the coupling step is performed at about 30-40 W for about 2 minutes

EXAMPLE 3

Radiolabel of HER-2 Targeting Peptide Using SPE-Purified [$^{18}$F]SFB

Figure 5:
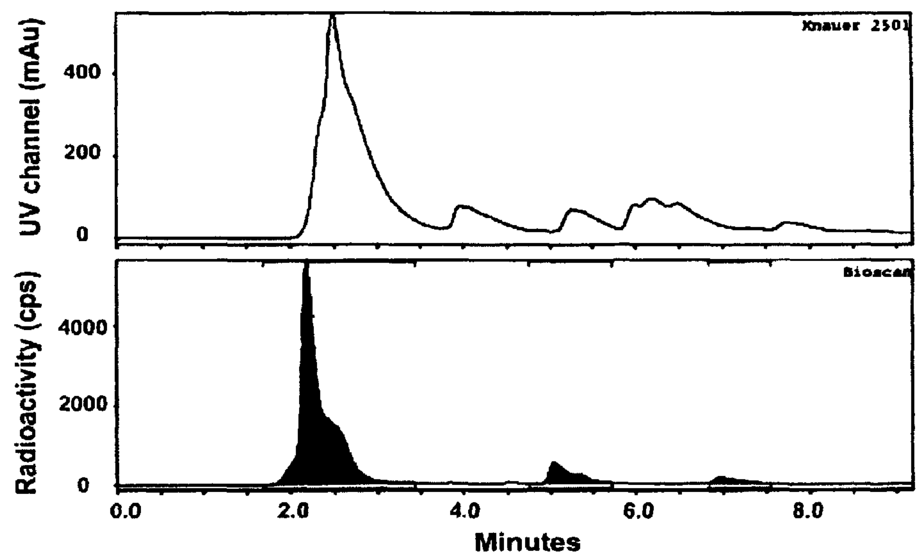
FIG. 5 shows the UV (upper graph) and radioactivity HPLC (lower graph) profiles of the reaction mixture of [$^{18}$F]SFB and [$^{18}$F]FB-labeled HER2-targeting peptide.

For peptide labeling, [$^{18}$F]SFB in PBS buffer (pH 7.4) was added to a solution of either the HER2 targeting peptide (KGSGKCCYSL, 5 mg/mL) or its scrambled version (KGSGKYLCSC) in pH 8.5 sodium borate buffer at a volume ratio of the two solutions of 5:1. The labeling reaction was performed for 45 min. Based on the radio-HPL chromatogram of the end product, the overall labeling yield of the corresponding $^{18}$F-labeled peptide is from about 60 to about 80% (FIG. 5). A part of the reaction mixture was then injected into a semi-preparative reversed-phase radio-HPLC system for further purification. The peak of the radiotrace that corresponded to the peptide retention time was collected. Afterwards, the total volume of the solution was reduced in a remotely controlled micro-rotary evaporator and it was diluted with saline solution ready for microPET study.

EXAMPLE 4

Radiolabel of Anti-HER2 Diabody Using SPE-Purified [$^{18}$F]SFB

Figure 7:
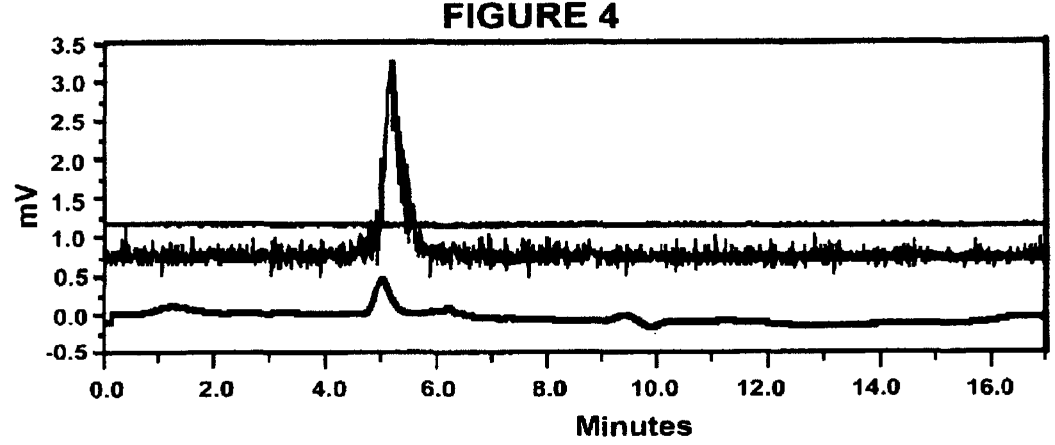
FIG. 7 are size exclusion chromatograms of a reaction mixture of [$^{18}$F]FB-labeled anti-HER2 diabody after microspin column purification. The radioactivity is shown by the upper curve; the lower curve is the UV-trace.
Figure 6:
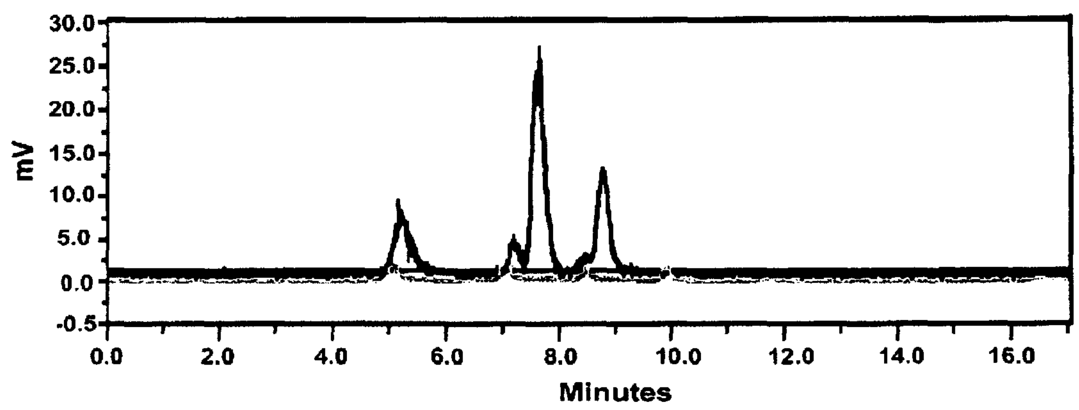
FIG. 6 are size-exclusion chromatograms of a reaction mixture of [$^{18}$F]SFB and [$^{18}$F]FB-labeled anti-HER2 diabody before microspin column purification. The radioactivity is shown by the upper curve; the lower curve is the UV-trace.

[$^{18}$F]SFB was added to an anti-HER2 diabody solution (600 μL) in sodium borate buffer (pH 8.5, 50 mM) and the reaction was allowed to proceed for 45 minutes. The radiolabeled conjugate was separated from free [$^{18}$F]SFB and [$^{18}$F]FBA using a Micro Biospin 6 chromatography column (Bio-Rad, Hercules, Calif.), which was pre-equilibrated with sodium borate buffer. A size exclusion chromatograms of the reaction mixture of [$^{18}$F]FB-labeled anti-HER2 diabody before and after microspin column purification is shown in FIG. 6 and FIG. 7 respectively. The radioactivity is shown by the upper curve; the lower curve is the UV-trace. Spin column separation was performed in 75 μL aliquots, which was the maximum column volume. An additional aliquot of radiolabeled diabody was subjected to size exclusion HPLC purification using a Jupiter 300 (C18; Phenomenex, Torrance, Calif.) column. Instant thin layer chromatography (ITLC; Biodex, Shirley, N.Y.) was used to determine radiochemical yield and specific activity per microliter of purified [$^{18}$F]FB-labeled diabody. 1 μL of conjugate was evaluated by instant thin layer chromatography followed by mobilization in normal saline. Strips were cut in half (bottom-bound radiolabel, top-free radiolabel) and counted on a gamma counter (Wizard 3, Perkin Elmer, Waltham, Mass.).

EXAMPLE 5

MicroPET Study

Figure 8:
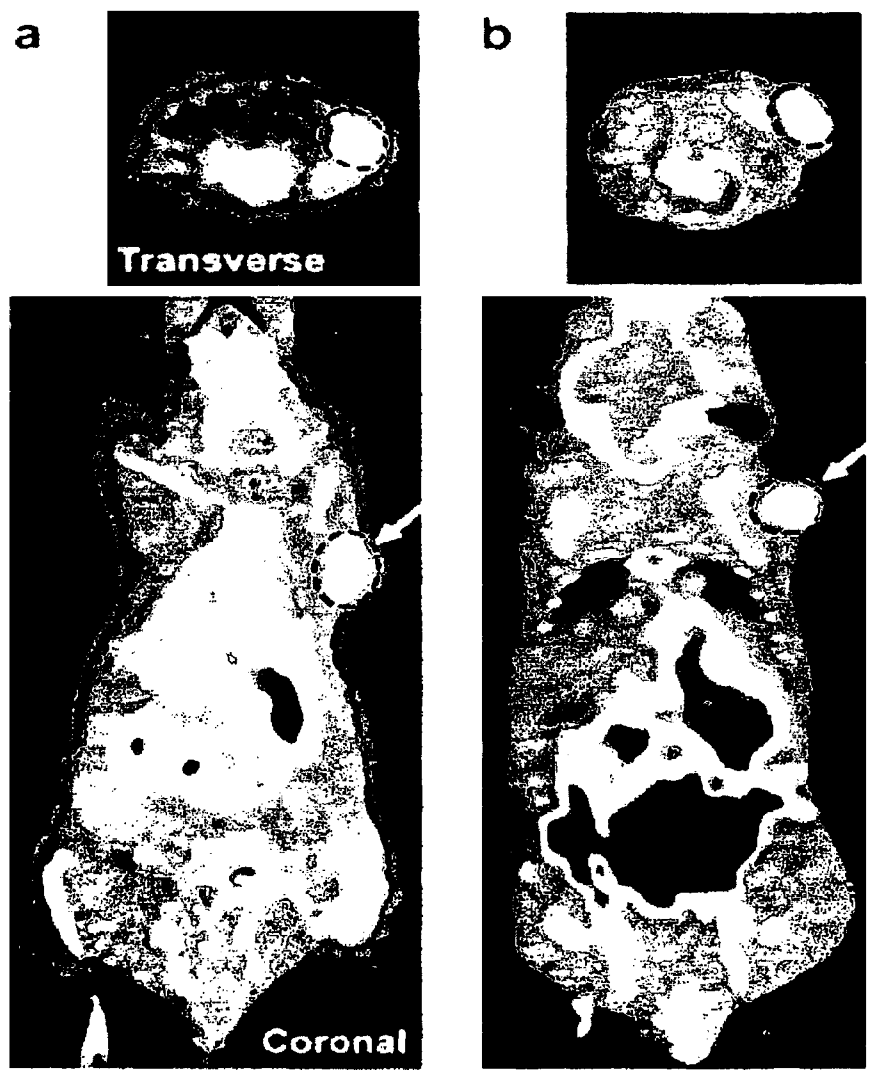
FIG. 8 is ImmunoPET/CT imaging of a mouse using [$^{18}$F]FB-labeled HER2 targeting peptide (left image) (2 hr post-injection) and anti-HER2 diabody (right image) (4 hr post-injection) in MCF7-HER2 xenograft. Tumors are encircled and indicated by the arrow.

For the micro-PET study, female nude mice (4 to 5 weeks old) were administrated estradiol pellets for two months, and then they were injected with tumor cells (MCF-7 ca $10^7$ cells) subcutaneously in the right flank. After tumor growing to ca. 1000 mm$^3$, the xenocraft-bearing mice were anesthetized with isoflurane in oxygen in an anesthesia bed, then injected with $^{18}$F-labeled HER-2 peptide produced in accordance with example 3 above, its scrambled analogs or a $^{18}$F-labeled diabody (40-80 μCi in 100 μL) produced in accordance with example 4 above via the lateral tail vein. The nude mice were imaged under anesthesia on a MicroPET Focus 220 scanner or Inveon (Siemens Preclinical Solutions, Knoxville, Tenn.). FIG. 8 shows the images obtained 2 hours and 4 hours post injection using 10-minute static acquisitions. The tumors are encircled and indicate by the arrows.

Figure 9:
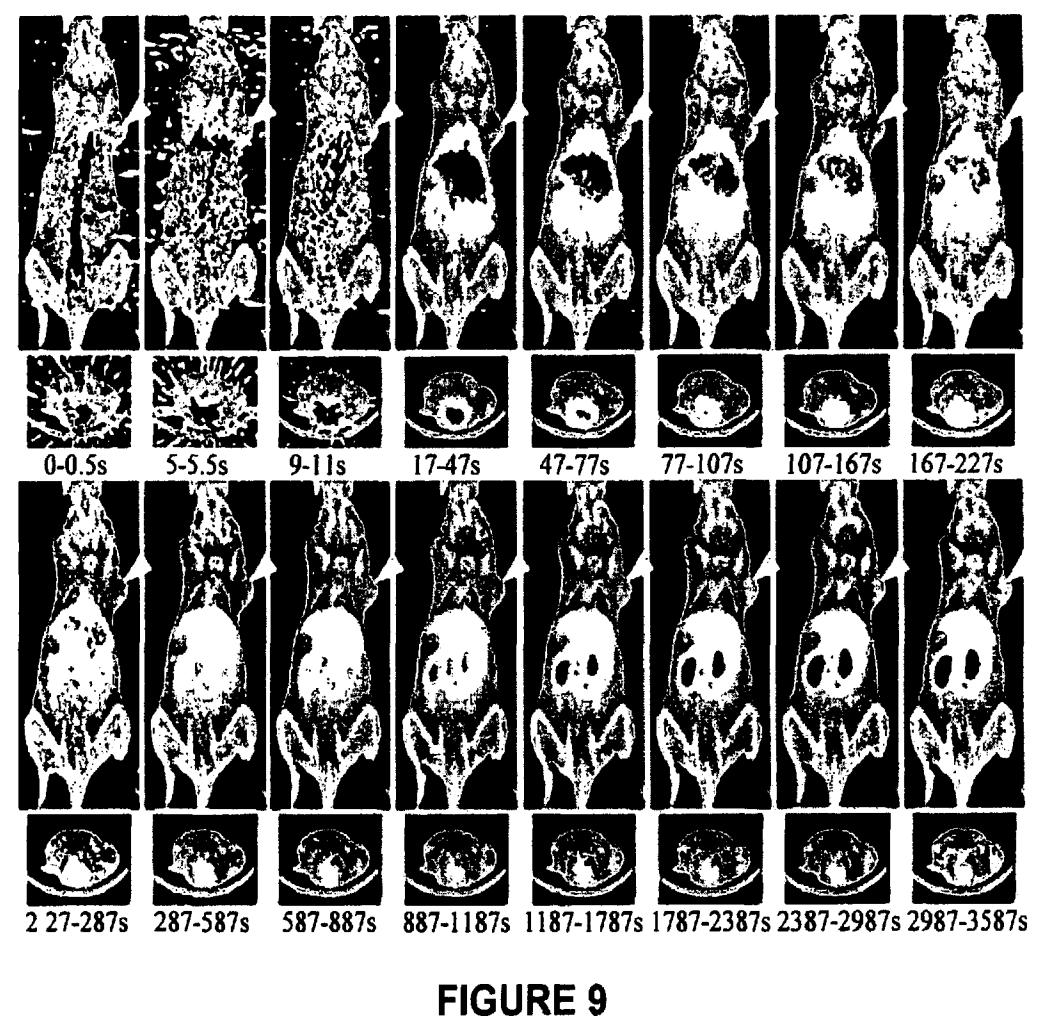

Shown in FIG. 9 are dynamic imaging using 10 s time frames initiated immediately prior to tail vein injection of the radiotracer. Dynamic 10 s time frames were continued over 10 minutes after injection. These were then followed by nine 5-minute time frame initiated ten minutes after injection. Images were reconstructed using filtered back projection or MAP iterative reconstruction. At the end of the experiment, the animal was transferred to the microCT scanner for a 7-minute scan.

As set forth above, N-Succinimidylester 4-[$^{18}$F fluorobenzoate ([$^{18}$F]SFB) is a well known compound that can be potentially used to radiolabel targeting ligands in diagnostic procedures, such as a PET scan, to locate diseased tissue within the body of animals, including humans. In such instances, [$^{18}$F]SFB is attached to a biomolecule, such as a protein, which is specifically attracted to the target tissue. Generally speaking, [$^{18}$F]SFB reacts with primary amine residues on aminoacids. That [$^{18}$F]SFB-labeled biomolecule is introduced into the body, typically into a blood vessel, usually by injection and allowed to migrate to the site of the target tissue which then becomes radioactive and can be detected using a radiation sensing scan or probe. While a primary use of such labeled biomolecules is to target cancerous tissue for location by a PET scan, the use of such radiation emitting biomolecules is not so limited. Targeted tissue within the body, once labeled by such radiolabeled biomolecules, can be located by interoperative radiation detection probes and less invasive probes introduced by laparoscopic procedures or on catheter tips. In addition, radiolabeled tissue is not limited to cancerous tissue and may include benign growths within the body as well as other abnormal physiological conditions such as the deposition of atheroslerotic plaque and the location of blood clots as well as neurodegenerative diseases.

While the invention described herein provides two examples incorporating features of the invention for the preparation [$^{18}$F]SFB, the subsequent labeling of a peptide or an engineered antibody fragment with [$^{18}$F]SFB and the use of the $^{18}$F labeled biomolecules to locate one or more tumors in a body, the invention set forth herein is not so limited.

While labeling of a peptide or HER2 were provided as examples of labeled biomolecules, other biomolecules can be labeled with [$^{18}$F]SFB in a similar manner. For example, [$^{18}$F]SFB can be used to label viruses, cells, peptides, proteins, antibodies, lipids, sugars, polymers, nanoparticles, including nanowires and nanorods and small molecules, for example drugs, which contain primary amines. Specific examples include, but are not limited to:

a) proteins—anti-HER2/anti-EGFR affibody, antiHER2/anti-HER 3 diabody, Annexin V and anti-CEA diabody and anti-CD66 antibody;

b) peptides—proinsulin connecting peptide, C-peptide, endothelin-1, α-MSH (α-melanocyte stimulating hormone) and its analogs, neurotensin, bombesin (BBN) and its analogs, vasoactive intestinal peptide (VIP) and its analogs, arginine-glycine-aspartic acid (RGD) peptide, BBN-RGD heterodimer, and its analogs, δ-opioid receptor antagonist and urortensin-II;

c) small molecules—prostate specific membrane antigen and (PSMA) inhibitor

Further, while the examples describe a non-aqueous saponification procedure for preparing [$^{18}$F]SFB, one skilled in the art will recognized, based on the teachings herein, that other radiolabeling compounds can be prepared using similar preparative techniques and these alternative radiocompounds can then be used to label biomolecules in the same manner as described above.

We claim:

1. An anhydrous process for preparing $^{18}$F labeled compounds comprising a labeling step comprising, reacting an alkyl or aryl 4-trimethylammoniumbenzoate triflate with a dried potassium-Kryptofix-2.2.2 complex salt of [$^{18}$F]fluoride, or a cesium salt of [$^{18}$F]fluoride, in dimethylsulfoxide (DMSO), to provide a corresponding alkyl or aryl 4-[$^{18}$F]fluorobenzoate solution, a deprotecting step comprising dissolving the alkyl or aryl 4-[$^{18}$F]fluorobenzoate in a basic anhydrous/aprotic solvent to provide a reaction mixture containing 4-[$^{18}$F] fluorobenzoate salt, and a coupling step comprising adding a solution of an activating agent to the reaction mixture contained 4-[$^{18}$F]fluorobenzoate to provide an activated ester wherein the process include reacting the activated ester with a primary amine containing compound to provide a radiolabeled compound.

2. The process of claims 1 wherein the activating agent is, O—(N-succinimidyl)-N,N,N',N'-tetramethyluronium tetrafluoroborate, N-succinimidyl 4-[$^{18}$F]fluorobenzoate ([$^{18}$F] SFB) is formed, dissolved in a solvent and is purified by using a solid phase extraction system, the [$^{18}$F]SFB then being eluted from the solid phase extraction system.

3. The process of claim 2 wherein the solvent is a weak acidic aqueous solution.

4. The process of claim 3 wherein the weak acidic aqueous solution is an acetic acid solution.

5. The process of claim 2 wherein the [$^{18}$F]SFB is eluted using an organic solvent.

6. The process of claim 5 wherein the organic solvent is ethyl ether.

7. The process of claim 2 further including reacting the [$^{18}$F]SFB with a primary amine containing compound to provide a radiolabeled compound.

8. The process of claim 7 wherein the primary amine containing compound is a virus, cell, peptide, protein, lipid, sugar, polymer, nanoparticle, nanowire, nanorod, small molecule or drug.

9. The process of claim 7 wherein the primary amine containing compound is a protein selected from the group consisting of an anti-HER/anti-EGFR antibody, antiHER2/anti-HER 3 diabody, Annexin V and anti-CEA diabody and anti-C066 antibody, a peptide selected from the group consisting of a proinsulin connecting peptide, C-peptide, endothelin-1, α-melanocyte stimulating hormone and its analogs, neurotensin, bombesin and its analogs, vasoactive intestinal peptide and its analogs, arginine-glycine-aspartic acid peptide, BBN-RGD heterodimer and its analogs, (δ-opoid receptor antagonist and urortensin-II; and small molecules selected from the group consisting of prostate specific membrane antigen and (PSMA) inhibitor.

10. The process of claim 2 wherein the alkyl is selected from the group consisting of methyl, ethyl, i-propyl and benzyl and the aryl is selected from the group consisting of phenyl and substituted phenyls. wherein the alkyl groups are methyl, ethyl, i-propyl or benzyl and the aryl groups are phenyl or substituted phenyls.

11. The process of claim 1 wherein the labeling step is conducted at 90-100° C. for 5-15 minutes, the deprotection step is conducted at from about 90° C. to about 100° C. for about 5-10 minutes and the coupling step is conducted at 85° C-90° C. for about 9-10minutes, the heat being provide by a heat source external to a reaction vial containing the reaction mixture.

12. The process of claim 1 wherein a microwave source provides energy for the labeling, deprotection and coupling step and the labeling step is conducted with the microwave source operating at 20W-60W for 1-3 min, the deprotection step is conducted with the microwave source operating at about 40W-50W for about 1minute and the coupling step is performed with the microwave source operating at about 30-40W for about 2 minutes.

13. The process of claim 1 wherein the primary amine containing compound is a virus, cell, peptide, protein, lipid, sugar, polymer, nanoparticle, nanowire, nanorod, small molecule or drug.

14. The process of claim 1 wherein the primary amine containing compound is a protein selected from the group consisting of an anti-HER/anti-EGFR antibody, antiHER2/anti-HER 3 diabody, Annexin V and anti-CEA diabody and anti-C066 antibody, a peptide selected from the group consisting of a proinsulin connecting peptide, C-peptide, endothelin-1, αmelanocyte stimulating hormone and its analogs, neurotensin, bombesin and its analogs, vasoactive intestinal peptide and its analogs, arginine-glycine-aspartic acid peptide, BBN-RGD heterodimer and its analogs, (δ-opoid receptor antagonist and urortensin-II; and small molecules selected from the group consisting of prostate specific membrane antigen and (PSMA) inhibitor.

15. The process of claim 1 wherein the alkyl is selected from the group consisting of methyl, ethyl, i-propyl and benzyl and the aryl is selected from the group consisting of phenyl and substituted phenyls.

16. The process of claim 1 wherein the alkyl or aryl 4-trimethyl-ammoniumbenzoate triflate is ethyl 4-trimethylammoniumbenzoate triflate.

17. The process of claim 1 wherein the basic anhydrous/aprotic solvent is selected from the group consisting of potassium tert-butoxide (t-BuOK) in anhydrous DMSO, LiCl in DMF or pyridine, NaCN in DMSO, $KO_2$, 18-crown-6 in benzene, LiCl in EtOAc, TMSCl or NaI in MeCN, $MgI_2$ in toluene or $(Bu_3Sn)_2O$ in benzene.

18. The process of claim 1 wherein the weak acidic aqueous solution is an acetic acid solution.

19. The process of claim 18 wherein the organic solvent is ethyl ether.

* * * * *